United States Patent [19]

Castillo et al.

[11] Patent Number: 6,077,880

[45] Date of Patent: Jun. 20, 2000

[54] HIGHLY RADIOPAQUE POLYOLEFINS AND METHOD FOR MAKING THE SAME

[75] Inventors: Miguel Castillo, Hialeah; Joquin Villalobos, Miami; Jeffrey Walker, Fort Lauderdale, all of Fla.

[73] Assignee: Cordis Corporation, Miami, Fla.

[21] Appl. No.: 09/120,414

[22] Filed: Jul. 22, 1998

Related U.S. Application Data

[62] Division of application No. 08/907,467, Aug. 8, 1997, abandoned.

[51] Int. Cl.[7] .............................. C08J 7/04; A61L 29/18; A61L 29/08
[52] U.S. Cl. ........................ 523/105; 524/398; 524/440; 524/586; 604/523
[58] Field of Search ............................. 523/105; 524/440, 524/398, 586; 604/523

[56] References Cited

U.S. PATENT DOCUMENTS

| | | | |
|---|---|---|---|
| 2,462,331 | 2/1949 | Myers | 260/23 |
| 3,867,315 | 2/1975 | Tigner | 252/512 |
| 4,000,739 | 1/1977 | Stevens | 128/214 |
| 5,045,072 | 9/1991 | Castillo | 604/280 |
| 5,300,048 | 4/1994 | Drewes | 604/280 |
| 5,453,095 | 9/1995 | Davila | 604/167 |

FOREIGN PATENT DOCUMENTS

| | | |
|---|---|---|
| 0 365 399 | 12/1989 | European Pat. Off. ........... C08J 3/22 |
| 0 546 546 | 6/1993 | European Pat. Off. . |
| 0 624 380 | 4/1994 | European Pat. Off. ....... A61M 25/01 |
| WO 93/05101 | 3/1993 | WIPO . |

*Primary Examiner*—Andrew E. C. Merriam
*Attorney, Agent, or Firm*—Dean Garner

[57] ABSTRACT

In accordance with the present invention there is provided a method for making a highly radiopaque polyolefin compound, wherein the radiopaque material in said compound is substantially uniformly dispersed and held within a polymer matrix. During the method one first heats an amount of polyolefin, preferably low density polyethylene, to at least its melting temperature. The amount of polyolefin is equal to at least 10% by weight of the compound. Then an amount of radiopaque metal powder is added to the polyolefin. The amount of radiopaque metal is equal to up to 90% by weight of the compound. The metal powder is preferably tantalum, tungsten, gold or platinum. Thereafter, an amount of a dispersing agent is added to the polyolefin to form a mixture. The amount of dispersing agent is equal to at least 0.2% by weight of the compound. The dispersing agent is preferably zinc stearate, aluminum stearate or calcium stearate. Lastly, the mixture is mixed and cooled below its melting temperature to form the compound.

13 Claims, 1 Drawing Sheet

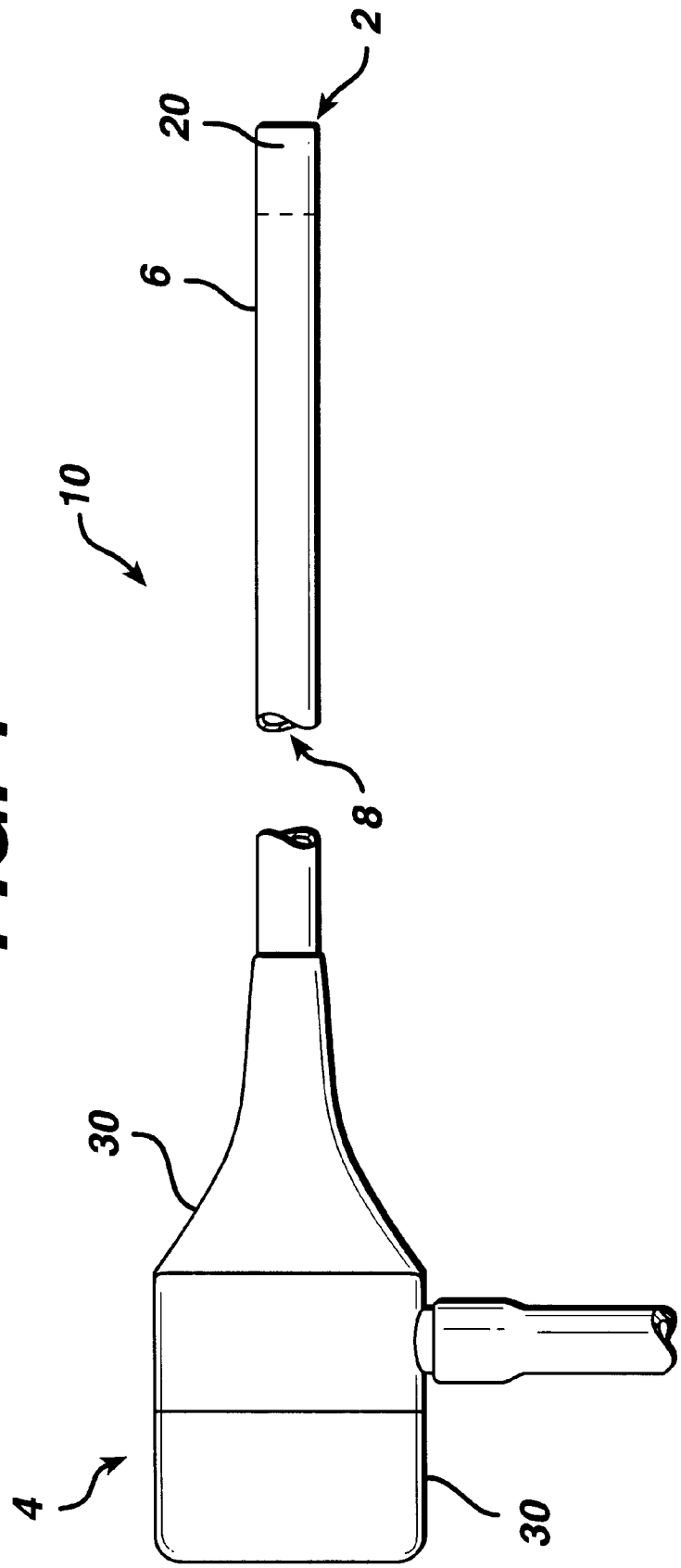

HIGHLY RADIOPAQUE POLYOLEFINS AND METHOD FOR MAKING THE SAME

This application is a division of U.S. application Ser. No. 08/907,467, filed on Aug. 08, 1997, now abandoned.

FIELD OF THE INVENTION

The present invention relates to highly radiopaque polyolefins and methods for making the same. The present invention has even further relation to medical devices such as catheters, having such highly radiopaque polyolefins at their distal tip.

BACKGROUND OF THE INVENTION

Catheters, such as guiding catheters and catheter sheath introducers, used in angioplasty procedures are typically made from polymers such as polyurethane. It is often desirable that the distal tips of these catheters be radiopaque, so they are clearly visible under fluoroscope. This aids the physician in performing the angioplasty or other like procedure. An example of a prior art catheter having a radiopaque tip is found in U.S. Pat. No. 5,045,072 issued to Castillo et al. on Sep. 3, 1991, which is hereby incorporated herein by reference.

The distal tips of catheters are typically made of a polyether polyurethane formulation having a radiopaque filler such as bismuth trioxide. An example of one formulation contains 39.7 weight percent of a commercially available polyurethane (Pellethane 80AE, sold by the Dow Chemical Company); 60 weight percent of bismuth trioxide: and 0.3 weight percent of oxidized polyethylene, which is a commercially available and known dispersing agent, release agent, and lubricant for the system.

Recently, there has been a desire to make a catheter which has greater radiopacity than those now currently available. The more easily the physician can see the catheter tip under fluoroscope, the easier it is to perform the procedure and accurately locate the catheter within the body. However, when adding large amounts of radiopaque agents, such as bismuth trioxide, to polymers, the compound begins to degrade and lose many of the desired physical mechanical properties.

An example of an attempt to overcome the above difficulties and make a more radiopaque polymer distal tip for a catheter is given in U.S. Pat. No. 5,300,048 issued to Drewes et al. on Apr. 5, 1994, which is hereby incorporated herein by reference. This type a catheter uses a polymer, such as a polyether block amide. In order to make the composition more radiopaque, a compound having higher radiopacity per volume amount than bismuth trioxide was used. For example they used metal powders such as tungsten, platinum, gold, silver, lead and tantalum, in amounts greater than 75 weight percent and up to 95 weight percent. However, it has been found that in such a compound the radiopaque metal is not properly wetted and uniformly dispersed within the polymer, and in addition does not bond and seal well with the polymer. Therefore, it runs the risk of degrading and having particulates of radiopaque metal fall off. In addition, adding any of the known dispersing agents in this field, such as oxidized polyethylene, to such a compound does not effectively solve the problem. Those types of dispersing agents do not sufficiently bond and seal the metal within the polymer. Even with dispersing agents, some polymers, such as polyurethane, suffer a catalytic effect when large amounts of metals, especially bismuth compounds, are compounded with it.

Adding large amounts of metal powders to certain polymers can either cause them to degrade or not sufficiently bond to the polymer. Adding large amounts of other radiopaque agents, such as bismuth trioxide, does not work either. There has, therefore, been a need for a polymer compound which is more radiopaque than those described in the prior art. There has also been a need for such a compound wherein the radiopaque material is uniformly dispersed within the compound. There has also been a need for such a compound wherein the radiopaque material is bonded to and sealed with the polymer so that the risk of radiopaque particulate material becoming loose during the use of the product is minimized. The present invention is intended to fulfill such needs.

SUMMARY OF THE INVENTION

In accordance with the present invention there is provided for making a highly radiopaque polyolefin compound, wherein the radiopaque material in said compound is substantially uniformly dispersed and held within a polymer matrix. During the method, one first heats an amount of polyolefin, preferably low density polyethylene, to at least its melting temperature. The amount of polyolefin is equal to at least 10% by weight of the compound. Then an amount of radiopaque metal powder is added to the polyolefin. The amount of radiopaque metal is equal to up to 90% by weight of the compound. The metal powder is preferably tantalum, tungsten, gold or platinum. Thereafter, an amount of a stearate dispersing agent is added to the polyolefin to form a mixture. The amount of dispersing agent is equal to at least 0.2% by weight of the compound. The dispersing agent is preferably zinc stearate, aluminum stearate or calcium stearate. Lastly, the mixture is mixed and cooled below its melting temperature to form the compound. Also, in accordance with the present invention is a compound made in accordance with the previously described method.

It has been discovered that the use of a polyolefin in combination with a highly radiopaque metal along with a dispersing agent made from a stearate forms a radiopaque polymer compound that is more radiopaque than those currently available for such uses as catheters. In addition, this compound is stable and the metal powder is uniformly dispersed throughout and kept bonded well within the compound. In addition to a method of making the compound, the present invention includes compound itself which is described herein as well.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

FIG. 1 is a plan view of a catheter sheath introducer having a distal tip made in accordance with the present invention.

DETAILED DESCRIPTION OF THE INVENTION

Referring to the drawings wherein like numerals indicate the same elements throughout the views, there is shown in FIG. 1 a catheter sheath introducer, or catheter, 10 having a highly radiopaque distal tip 20 made in accordance with the present invention. Examples of catheter sheath introducers can be found in U.S. Pat. No. 5,453,095 issued to Davila et al. on Sep. 26, 1995, and U.S. Pat. No. 4,000,739 issued to Stevens on Jan. 4, 1977, both of which are hereby incorporated herein by reference. Catheter 10 has a distal end 2 and a proximal end 4. Catheter 10 includes an elongated tubular body 6 having a lumen 8 therein. Body 6 is preferably made from the same base polyolefin that the tip is made from, such as polyurethane, so that the tip can be securely bonded to the body. The proximal end 4 of catheter 10 includes a housing 30. As is well known by those skilled in the art, the housing 30 typically includes a homeostasis valve, not shown. A catheter sheath introducer is typically inserted into the femoral artery of a patient in order to gain access to the vascular system. The housing and valve remain outside the patient and allows a physician to insert and exchange other catheters, guidewires stents or the like into the housing and through body 6 so they can then enter the human vasculature. The particular example of a catheter shown in FIG. 1 is that of a catheter sheath introducer. However, as will be appreciated by those skilled in the art, the technology described herein can readily be applied to making radiopaque distal tips for guiding catheters, diagnostic catheters, micro-catheters or the like. In fact the present invention has application to any device which uses a radiopaque polymer. Especially, if such use is to use the radiopaque polymer as a clearly visible marker under fluoroscopy.

As mentioned above, catheter 10 includes a highly radiopaque distal tip 20. Distal tip 20 is made from a polyolefin compound. The compound preferably contains up to 10 weight percent, and more preferably 30–60 weight percent, of a polyolefin such as low density polyethylene, up to 90 weight percent, and more preferably 39–69 weight percent, radiopaque metal powder, such as tantalum, tungsten, gold and platinum, and at least 0.2 weight percent, and more preferably 0.4–1.1 weight percent, stearate dispersing agent, preferably a metal stearate such as zinc stearate, aluminum stearate and calcium stearate. As will be described below, the method used in making such a compound results in the metal powder is substantially uniformly distributed and held within a polymer matrix. Polymer matrix being a commonly known term by those skilled in the art and generally referring to the network of polymer material surrounding the other compound ingredients. In addition, the present method results in a compound wherein the radiopaque metal powder is properly wetted with the dispersing agent, i.e. the metal stearate, while in the polymer matrix. Such terminology is common to those of ordinary skill in the art. The radiopaque metal is coated with the dispersing so that in fills in any gaps that might normally exist between a compound of the metal and polymer without the dispersing agent.

The method of making the highly radiopaque polyolefin compound of the present invention comprises the steps of heating the polyolefin material to at least its melting temperature, adding the radiopaque metal powder to said polyolefin, and adding the stearate dispersing agent to said polyolefin to form a mixture. Thereafter the polyolefin is mixed and cooled below its melting temperature, thereby forming the compound. The amounts of each substance in the material should be in accordance with the weight percent amounts discussed above. It has been discovered that the use of a polyolefin in combination with a highly radiopaque metal powder along with a dispersing agent made from a stearate forms a radiopaque polymer compound having superior physical properties and that is more radiopaque than those currently available for uses as catheters. In addition, this compound is stable and the metal powder is uniformly dispersed throughout and kept bonded well within the compound.

After the compound is formed it can then be cut into pellets and extruded into a desired form. One particular use would be to extrude the compound into a tubular form for making tip 20 of catheter 10. Such techniques are currently done with prior art radiopaque polymers, and are well known to those of ordinary skill in the art. Thereafter, the tubular tip of the catheter can be fused onto the tubular body to make the catheter or catheter sheath introducer. Such manufacturing methods are well known to those of ordinary skill in the art.

Examples of how to make a compound in accordance with the present invention are given below.

EXAMPLE 1

For making the compound one can preferably use any commercially available twin extruder, such as a 40 mm twin extruder, model #ZSKW&P, available from Wernerpflidrer located in both Ramsey, N.J. and Stuggart, Germany. The extruder can then preferably be heated to between about 360° F. (182° C.) to about 420° F. (215° C.). Commercially available granulated low density polyethylene can be fed into the upstream hopper of the extruder at a rate 30–60 pounds (13.6–27.3 kg) per hour such that the polyethylene. Thereafter a mixture of between 39 to 69 parts by weight commercially available tungsten powder and 0.4 to 1.1 parts by weight commercially available powdered zinc stearate can be fed into a downstream hopper at a rate of 40–70 pounds per hour where the polyethylene has achieved a temperature between about 360° F. to about 420° F. Downstream of the second hopper, after the compound has sufficiently and thoroughly mixed together, the compound can be extruded into thin strands and placed in a water bath to cool to about room temperature. Thereafter, the strands can be cut into pellets and extruded into tubing for the manufacture of catheters. Such extrusion and manufacturing methods are well known to those of ordinary skill in the art.

EXAMPLE 2

In another way for making the compound, one can preferably use any commercially available Bambury Mixer, such as model # 00, available from the Bolling Company located in Cleveland, Ohio. The twin rotating blades of the mixer can be started, and sufficient pressure can be applied to the mixing chamber so that the chamber reaches a temperature between about 360° F. to about 420° F. Commercially available granulated low density polyethylene in an amount between 30–60 pounds, commercially available tungsten powder in an amount between 39–69 pounds, and commercially available zinc stearate powder in an amount between 0.4 and 1.1 pounds can be fed into the mixing chamber. The ingredients can then be allowed to mix for a sufficient time in order to thoroughly mix them. The compound can then be removed from the mixer and passed through a double mill roll to flatten the compound. The compound can then be allowed to cool to room temperature. Thereafter, the compound can be cut into pellets and extruded into tubing for the manufacture of catheters. Such extrusion and manufacturing methods are well known to those of ordinary skill in the art.

EXAMPLE 3

For making the compound one can preferably use any commercially available twin extruder, such as 40 mm twin extruder, model # ZSKW&P, available from Wernerpflidrer located in both Ramsey, N.J. and Stuggart, Germany. The extruder can then preferably be heated to between about 360° F. (182° C.) to about 420° F. (215° C. Commercially available granulated low density polyethylene, preferably Tenite PE 800A available from Union Carbide, can be fed into the upstream hopper of the extruder at a rate of 60 pounds per hour such that the polyethylene. Thereafter a mixture of 79 parts by weight available tungsten powder and 1 part by weight commercially available powdered zinc stearate can be fed into a downstream hopper, at a rate of 40 pounds per hour, where the polyethylene has achieved a temperature between about 360° F. to about 420° F. Downstream of the second hopper, after the compound has sufficiently and thoroughly mixed together, the compound can be extruded into thin strands and placed in a water bath to cool to about room temperature. Thereafter, the strands can be cut into pellets and extruded into tubing for the manufacture of catheters. Such extrusion and manufacturing methods are well known to those of ordinary skill in the art.

EXAMPLE 4

For making the compound one can preferably use any commercially available twin extruder, such as a 40 mm twin extruder, model # ZSKW&P, available from Wernerpflidrer located in both Ramsey, N.J. and Stuggart, Germany. The extruder can then preferably be heated to between about 360° F. (182° C.) to about 420° F. (215° C.) Commercially available granulated low density polyethylene, preferably Tenite PE 800A available from Union Carbide, can be fed into the upstream hopper of the extruder at a rate of 50 pounds per hour such that the polyethylene. Thereafter a mixture of 70.43 parts by weight commercially available tungsten powder and 1 part by weight commercially available powdered zinc stearate can be fed into a downstream hopper at a rate of 50 pounds per hour where the polyethylene has achieved a temperature between about 360° F. to about 420° F. Downstream of the second hopper, after the compound has sufficiently and thoroughly mixed together, the compound can be extruded into thin strands and placed in a water bath to cool to about room temperature. Thereafter, the strands can be cut into pellets and extruded into tubing for the manufacture of catheters. Such extrusion and manufacturing methods are well known to those of ordinary skill in the art.

EXAMPLE 5

For making the compound one can preferably use any commercially available twin extruder, such as a 40 mm twin extruder, model # ZSKW&P, available from Wernerpflidrer located in both Ramsey, N.J. and Stuggart, Germany. The extruder can then preferably be heated to between about 360° F. (182° C.) to about 420° F. (215° C.). Commercially available granulated low density polyethylene, preferably Tenite PE 800A available from Union Carbide, can be fed into the upstream hopper of the extruder at a rate of 40 pounds per hour such that the polyethylene. Thereafter a mixture of 65.67 parts by weight commercially available tungsten powder and 1 part by weight percent commercially available powdered zinc stearate can be fed into a downstream hopper at a rate of 60 pounds per hour where the polyethylene has achieved a temperature between about 360° F. to about 420° F. Downstream of the second hopper, after the compound has sufficiently and thoroughly mixed together, the compound can be extruded into thin strands and placed in a water bath to cool to about room temperature. Thereafter, the strands can be cut into pellets and extruded into tubing for the manufacture of catheters. Such extrusion and manufacturing methods are well known to those of ordinary skill in the art.

EXAMPLE 6

For making the compound one can preferably use any commercially available twin extruder, such as a 40 mm twin extruder, model # ZSKW&P, available from Wernerpflidrer located in both Ramsey, N.J. and Stuggart, Germany. The extruder can then preferably be heated to between about 360° F. (182° C.) to about 420° F. (215° C.). Commercially available granulated low density polyethylene, preferably Tenite PE 800A available from Union Carbide, can be fed into the upstream hopper of the extruder at a rate of 30 pounds per hour such that the polyethylene. Thereafter a mixture of 62.67 parts by weight commercially available tungsten powder and 1 part by weight percent commercially available powdered zinc stearate can be fed into a downstream hopper at a rate of 70 pounds per hour where the polyethylene has achieved a temperature between about 360° F. to about 420° F. Downstream of the second hopper, after the compound has sufficiently and thoroughly mixed together, the compound can be extruded into thin strands and placed in a water bath to cool to about room temperature. Thereafter, the strands can be cut into pellets and extruded into tubing for the manufacture of catheters. Such extrusion and manufacturing methods are well known to those of ordinary skill in the art.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A vascular catheter having a distal end and a proximal end, said distal end of said catheter comprising a highly radiopaque polyolefin compound wherein the radiopaque material in said compound is wetted with a dispersing agent and substantially uniformly dispersed and held within a polymer matrix, said highly radiopaque polyolefin compound is formed from a method comprising:
   a) heating an amount of polyolefin material to at least its melting temperature, said amount of polyolefin equal to at least 10% by weight of said compound;
   b) adding an amount of radiopaque metal powder to said polyolefin, said amount of radiopaque material equal to up to 90% by weight of said compound;
   c) adding an amount of a stearate dispersing agent to said polyolefin to form a mixture, said amount of metal stearate equal to at least 0.2% by weight of said compound; and
   d) mixing and cooling said mixture below its melting temperature to form said compound.

2. A vascular catheter having distal and proximal ends, wherein said distal end of said catheter comprises a radiopaque compound comprising up to 10% by weight polyolefin, up to 90% by weight radiopaque metal powder and at least 0.2% by weight stearate dispersing agent, wherein said metal powder is wetted with said dispersing agent and substantially uniformly distributed and held within a polymer dispersing agent and substantially uniformly distributed and held within a polymer matrix.

3. A vascular catheter having distal and proximal ends, wherein said distal end of said catheter comprises a radiopaque compound comprising up to 10% by weight low density polyethylene, up to 90% by weight radiopaque metal powder selected from the group comprising tantalum, tungsten, gold and platinum, and at least 0.2% by weight stearate dispersing agent selected from the group comprising zinc stearate, aluminum stearate and calcium stearate, wherein said metal powder is wetted with said dispersing agent and substantially uniformly distributed and held within a polymer matrix.

4. The vascular catheter according to claim 1 wherein said polyolefin comprises low density polyethylene.

5. The vascular catheter of claim 1 wherein said metal powder is selected from the group comprising tantalum, tungsten, gold and platinum.

6. The vascular catheter of claim 1 wherein said stearate dispersing agent selected from the group comprising zinc stearate, aluminum stearate and calcium stearate.

7. The vascular catheter of claim 1 wherein said polyolefin is heated between about 360° F. to about 420° F.

8. The vascular catheter of claim 1 wherein the weight percent of polyolefin is preferably between about 30–60, the weight percent of metal powder is preferably between about 39–69, and the weight percent stearate dispersing agent is between about 0.4–1.1.

9. The vascular catheter of claim 2 wherein the weight percent of polyolefin is preferably between about 30–60, the weight percent of metal powder is preferably between about 39–69, and the weight percent stearate dispersing agent is between about 0.4–1.1.

10. The vascular catheter according to claim 2 wherein said polyolefin comprises low density polyethylene.

11. The vascular catheter according to claim 2 wherein said metal powder is selected from the group comprising tantalum, tungsten, gold and platinum.

12. The vascular catheter according to claim 2 wherein said stearate dispersing agent selected from the group comprising zinc stearate, aluminum stearate and calcium stearate.

13. The vascular catheter of claim 3 wherein the weight percent of polyolefin is preferable between about 30–60, the weight percent of metal powder is preferably between about 39–69, and the weight percent stearate dispersing agent is between about 0.4–1.1.

* * * * *